(12) United States Patent
Sugihara et al.

(10) Patent No.: US 11,493,459 B2
(45) Date of Patent: Nov. 8, 2022

(54) INSPECTION METHOD AND MANUFACTURING METHOD FOR MOLDED RESIN PRODUCT AS WELL AS INSPECTION DEVICE AND MANUFACTURING DEVICE FOR MOLDED RESIN PRODUCT

(71) Applicant: Toray Industries, Inc., Tokyo (JP)

(72) Inventors: Hiroki Sugihara, Otsu (JP); Takahiro Tanino, Otsu (JP)

(73) Assignee: Toray Industries, Inc., Tokyo (JP)

( * ) Notice: Subject to any disclaimer, the term of this patent is extended or adjusted under 35 U.S.C. 154(b) by 334 days.

(21) Appl. No.: 16/757,519

(22) PCT Filed: Sep. 28, 2018

(86) PCT No.: PCT/JP2018/036280
§ 371 (c)(1),
(2) Date: Apr. 20, 2020

(87) PCT Pub. No.: WO2019/082596
PCT Pub. Date: May 2, 2019

(65) Prior Publication Data
US 2020/0249180 A1    Aug. 6, 2020

(30) Foreign Application Priority Data
Oct. 23, 2017    (JP) .............................. JP2017-204185

(51) Int. Cl.
*G01N 23/04*    (2018.01)
*G01N 23/18*    (2018.01)
(Continued)

(52) U.S. Cl.
CPC ........... *G01N 23/18* (2013.01); *B29D 22/003* (2013.01); *F17C 1/16* (2013.01); *G01N 23/04* (2013.01);
(Continued)

(58) Field of Classification Search
CPC ....... A61B 6/466; A61B 6/485; A61B 6/5211; A61B 6/469; A61B 6/461; A61B 6/504;
(Continued)

(56) References Cited

U.S. PATENT DOCUMENTS 5,085,343 A    2/1992   Scarr
7,035,450 B1   4/2006   Muller et al.
(Continued)

FOREIGN PATENT DOCUMENTS

JP    04009606 A    1/1990
JP    0293353 A     4/1990
(Continued)

OTHER PUBLICATIONS

International Search Report and Written Opinion for International Application No. PCT/JP2018/036280, dated Dec. 18, 2018, 5 pages. 2020.

*Primary Examiner* — Irakli Kiknadze
(74) *Attorney, Agent, or Firm* — RatnerPrestia

(57) ABSTRACT

For the purpose of enabling high-accuracy detection as to whether a molded resin product is a non-defective product or a defective product and advance detection of a molded resin product that may suffer deformation or the like in the future, the present invention relates to an inspection method and a manufacturing method for a molded resin product as well as an inspection device and a manufacturing device for a molded resin product, wherein, in an inspection of a joint interface of a molded resin product divided into a plurality of members, the height positions of defect candidates are measured from the results of detecting X rays radiated via at least two paths when the X rays are transmitted through the molded resin product, which makes it possible to detect a defect with high accuracy.

14 Claims, 14 Drawing Sheets

(51) Int. Cl.
  *B29D 22/00* (2006.01)
  *F17C 1/16* (2006.01)
  *G01N 23/083* (2018.01)
  *H01M 8/04082* (2016.01)

(52) U.S. Cl.
  CPC ...... *G01N 23/083* (2013.01); *H01M 8/04201* (2013.01); *F17C 2203/066* (2013.01); *F17C 2209/2109* (2013.01); *F17C 2221/012* (2013.01); *F17C 2270/0184* (2013.01); *H01M 2250/20* (2013.01)

(58) Field of Classification Search
  CPC ........... A61B 6/12; A61B 6/487; A61B 6/022; A61B 6/502; A61B 6/5223; A61B 6/5217; A61B 6/5264; A61B 6/0487; A61B 5/418; A61B 5/415; A61B 5/0059; G06T 7/0012; G06T 7/74; G06T 2207/20076; G06T 2207/10116; G06T 2207/20224; G06T 2207/10012; G06T 2207/30101; G06T 2207/10121; G06T 11/008; G06T 15/08; G06T 7/0004; G06T 2207/30108; H04N 13/349; H04N 13/111; H04N 5/32; H04N 13/264; H04N 13/221; H04N 2013/0074; G16H 50/30; G06V 10/44; A61N 5/103; A61K 49/0017; G01N 23/04; G01N 23/18; G01N 33/442; G01N 23/16; G01N 23/083; G01N 23/087; G01N 21/896; G01N 2223/419; B29C 45/7686; B29C 45/768; B29C 45/0062; H01M 8/04201; H01M 50/417; H01M 50/403; G01B 11/0608; G01B 11/2518; G01B 15/00; G01B 21/20; G01B 11/30; G01B 2210/52
  USPC .............................................. 378/57, 61, 62
  See application file for complete search history.

(56) References Cited

U.S. PATENT DOCUMENTS

| 9,470,368 | B2 | 10/2016 | Dullaert et al. | |
|---|---|---|---|---|
| 2008/0056446 | A1 | 3/2008 | Tahara | |
| 2011/0298116 | A1* | 12/2011 | Mizusaki | H01L 23/3107 257/676 |
| 2016/0074910 | A1* | 3/2016 | Fujii | G01N 23/087 209/589 |
| 2016/0214346 | A1* | 7/2016 | Hatanaka | B29C 45/1642 |
| 2018/0120243 | A1* | 5/2018 | Yashima | G06T 7/0008 |
| 2019/0003990 | A1* | 1/2019 | Onishi | G01N 23/18 |

FOREIGN PATENT DOCUMENTS

| JP | 0626548 A | 9/1994 |
|---|---|---|
| JP | 11316197 A | 11/1999 |
| JP | 2004340606 A | 12/2004 |
| JP | 2006220424 A | 8/2006 |
| JP | 2010281649 A | 12/2010 |
| JP | 2014501818 A | 1/2014 |

* cited by examiner

INSPECTION METHOD AND MANUFACTURING METHOD FOR MOLDED RESIN PRODUCT AS WELL AS INSPECTION DEVICE AND MANUFACTURING DEVICE FOR MOLDED RESIN PRODUCT

CROSS REFERENCE TO RELATED APPLICATIONS

This is the U.S. National Phase application of PCT/JP2018/036280, filed Sep. 28, 2018, which claims priority to Japanese Patent Application No. 2017-204185, filed Oct. 23, 2017, the disclosures of each of these applications being incorporated herein by reference in their entireties for all purposes.

FIELD OF THE INVENTION

The present invention relates to an inspection method and a manufacturing method for molded resin articles, an inspection apparatus and a manufacturing apparatus for molded resin articles, and a manufacturing method and a manufacturing apparatus for high pressure tanks that serve for high accuracy inspection of molded resin articles to determine whether they are acceptable or unacceptable, and also relates to a molded resin article, a high pressure tank, and a fuel cell vehicle.

BACKGROUND OF THE INVENTION

In recent years, fuel cell vehicles have attracted attention as a solution to the depletion of petroleum fuels and the reduction of harmful gas emissions. A fuel cell vehicle incorporates, for example, a fuel cell that generates electricity through electrochemical reaction of hydrogen and oxygen in the air, and supplies the electricity generated by the fuel cell to a motor to provide driving force. When the fuel cell is a hydrogen cell, the automobile is equipped with a high pressure tank to contain hydrogen. For example, such a high pressure tank is composed mainly of a liner member made of resin and a fiber reinforced resin layer that covers the outside surface of the liner member. The liner member is made of resin, metal such as aluminum and iron, or the like. In particular, active efforts have been focused on liner members made of resin because of being light in weight and high in moldability to permit inexpensive production.

PRIOR ART DOCUMENTS

Patent Documents

Patent document 1: Published Japanese Translation of PCT International Publication JP 2014-501818
Patent document 2: Japanese Unexamined Patent Publication (Kokai) No. HEI-4-9606

SUMMARY OF THE INVENTION

However, a high pressure tank manufactured using the molded article described in Patent document 1 may suffer from deformation or the like when filling and releasing of high pressure gas (high pressure hydrogen gas in particular) is repeated, and this has often been a cause of deterioration in reliability. The cause of such a sudden abnormality is usually unknown with no inspection methods available.

Thus, as a result of intensive studies aiming to solve the above-mentioned problems, the present inventors have found that deformation or the like of such a tank are attributable to, for example, impurities and voids that exist in a portion where two molded resin parts that are prepared separately are joined. In the case of adopting a welding-based joining method that is commonly used for joining molded resin articles, a step of thrusting the joint portion is necessary in order to ensure sufficient welding. In this step, a swell of molten resin (hereinafter referred to as burr) is formed in the joint portion. Voids and impurities in the burr do not cause deformation or the like of the resin molded product. However, as in the inspection method described in Patent document 2, the inspection of the interior of a molded resin article has been commonly performed by determining whether there exist internal impurities or voids based on changes in the amount of X-ray transmitted. This embodiment is illustrated in FIG. 3. This gives a schematic diagram designed to explain a typical defect portion and a non-defect portion that cannot be distinguished by an inspection setup incorporating a common X-ray transmission imaging device. To simplify the description, this shows only the cross section of a part of the joint portion of the molded resin article 2 located nearer to the X-ray emission means 1. In this setup, the X-ray beam emitted from the X-ray emission means 1 passes through both the joint portion to be examined and the burr portion and accordingly, it is difficult to determine whether a change in transmission of X-ray emitted from the X-ray emission means 1 is attributed to voids or impurities in the joint portion or to voids or impurities in the burr portion. In addition, the use of X-ray beams emitted in a plurality of directions is often practiced to identify a position where a defect occurs, but it is also difficult to determine whether the portion is a burr portion or a joint portion from the position where the defect occurs.

The present invention was made in view of such conventional problems, and an object thereof is to provide an inspection method and a manufacturing method for molded resin articles, an inspection apparatus and a manufacturing apparatus for molded resin articles, and a manufacturing method and a manufacturing apparatus for high pressure tanks that serve for high accuracy inspection of molded resin articles to determine whether they are acceptable or unacceptable and preliminary detection of molded resin articles that are likely to undergo deformation or the like in the future, and also provide a molded resin article, a high pressure tank, and a fuel cell vehicle.

Thus, the inspection apparatus for molded resin articles according to an embodiment of the present invention that is designed for solving the above-mentioned problems includes an X-ray emission means for emitting X-ray beams through a plurality of paths, one or more X-ray detection means for detecting X-ray beams passing through a molded resin article, and an image processing means, the image processing means including a defect candidate detection means for detecting defect candidates based on two or more images acquired by the X-ray detection means, a height measuring means using a stereo matching method, an image computing means for performing logical multiplication of the image having recorded height position information obtained by the height measuring means and a defect candidate image obtained by the defect candidate detection means, and a selection means for deciding the state of the defect candidate from the height position.

In the molded resin article inspection apparatus according to the present invention, it is preferable for the selection means to include a distance setting means for setting the distance from the X-ray emission means to the molded resin article, an inspection range setting means for setting an inspection range based on the distance and the thickness of the molded resin article, and a defect judgment means for deciding that a defect candidate found in the inspection range is a defect.

In addition, in the inspection apparatus for molded resin articles, it is preferable for the distance setting means to include a distance input means for inputting a target distance from the X-ray emission means to the molded resin article, a distance measuring means for measuring the distance from the X-ray emission means to the molded resin article, and a distance correction means for calculating the difference between the input value entered by the distance input means and the measured value taken by the distance measuring means and making a correction based thereon so that the distance becomes equal to the input value.

Furthermore, in the inspection apparatus for molded resin articles, it is preferable for the X-ray emission means to include one or more X-ray emission means and an X-ray emitting position moving means for moving the one or more X-ray emission means so that X-ray beams are emitted from two or more different positions towards the molded resin article.

In addition, in the inspection apparatus for molded resin articles, it is preferable for the X-ray emission means to include one or more X-ray emission means and a molded resin article position moving means for moving the molded resin article to two or more positions.

Furthermore, in the inspection apparatus for molded resin articles according to the present invention, it is preferable for the molded resin article to be a member of the high pressure tank.

In addition, it is preferable for the manufacturing apparatus for molded resin articles according to the present invention to be provided with an inspection means that uses the inspection apparatus for molded resin articles, and a selection means for distinguishing molded resin articles judged to be unacceptable by the inspection means from molded resin articles judged to be acceptable.

Furthermore, it is preferable for the manufacturing apparatus for high pressure tanks according to the invention to be provided with an inspection means that uses the inspection apparatus for molded resin articles, a selection means for distinguishing molded resin articles judged to be unacceptable by the inspection means from molded resin articles judged to be acceptable, and an outer layer forming means for forming an outer layer for reinforcement on the molded resin articles judged to be acceptable.

Furthermore, the inspection method for molded resin articles according to an embodiment of the present invention to be used for solving the above-mentioned problems is designed to emit X-ray beams through a plurality of paths, detect X-ray beams transmitted through a molded resin article at one or more positions, detect a defect candidate in a detected X-ray image, measure the height by the stereo matching method, perform logical multiplication of the resulting height information image and the image obtained as a defect candidate, and judge the state of the defect candidate based on the height position.

In the inspection method for molded resin articles according to the present invention, it is preferable that the selection method is designed to set a distance from the X-ray emitting position to the molded resin article, set an inspection range based on the distance and the thickness of the molded resin article, and decide that a defect candidate found in the inspection range is a defect.

In addition, in the inspection method for molded resin articles according to the present invention, it is preferable that the distance setting method is designed to input a target distance from the X-ray emitting position to the molded resin article, measure the distance from the X-ray emitting position to the molded resin article, and calculate the difference between the input distance value and the measured distance value to make a correction based thereon so that the distance becomes equal to the input value.

Furthermore, in the inspection method for molded resin articles according to the present invention, it is preferable for the method for emitting X-ray beams through a plurality of paths to be designed to move the X-ray emitting position so that X-ray beams are emitted from two or more different positions towards the molded resin article.

In addition, in the inspection method for molded resin articles according to the present invention, it is preferable for the method for emitting X-ray beams through a plurality of paths to be designed to emit X-ray beams from one or more positions and move the molded resin article to two or more positions.

Furthermore, in the inspection method for molded resin articles according to the present invention, it is preferable for the molded resin article to be a member of the high pressure tank.

In addition, the manufacturing method for molded resin articles according to an embodiment of the present invention include an inspection step that uses the inspection method for molded resin articles, and a selection step for distinguishing molded resin articles judged to be unacceptable in the inspection step from molded resin articles judged to be acceptable.

Furthermore, the manufacturing method for high pressure tanks according to an embodiment of the present invention includes an inspection step that uses the inspection method for molded resin articles, a selection step for distinguishing molded resin articles judged to be unacceptable in the inspection step from molded resin articles judged to be acceptable, and an outer layer forming step for forming an outer layer for reinforcement on the molded resin articles judged to be acceptable.

In addition, the manufacturing method for fuel cell vehicles according to an embodiment of the present invention includes an inspection step that uses the inspection method for molded resin articles, a selection step for distinguishing molded resin articles judged to be unacceptable in the inspection step from molded resin articles judged to be acceptable, an outer layer forming step for forming an outer layer for reinforcement on the molded resin articles judged to be acceptable in order to provide a high pressure tank, and an installation step for installing the resulting high pressure tank on a chassis.

The present invention serves to provide an inspection method and a manufacturing method for molded resin articles, an inspection apparatus and a manufacturing apparatus for molded resin articles, and a manufacturing method and a manufacturing apparatus for high pressure tanks that serve for high accuracy inspection of molded resin articles to determine whether they are acceptable or unacceptable and preliminary detection of molded resin articles that are likely to undergo deformation or the like in the future, and also provide a molded resin article, a high pressure tank, and a fuel cell vehicle.

DETAILED DESCRIPTION OF EMBODIMENTS OF THE INVENTION

<Inspection Apparatus for Molded Resin Articles>

Figure 1:
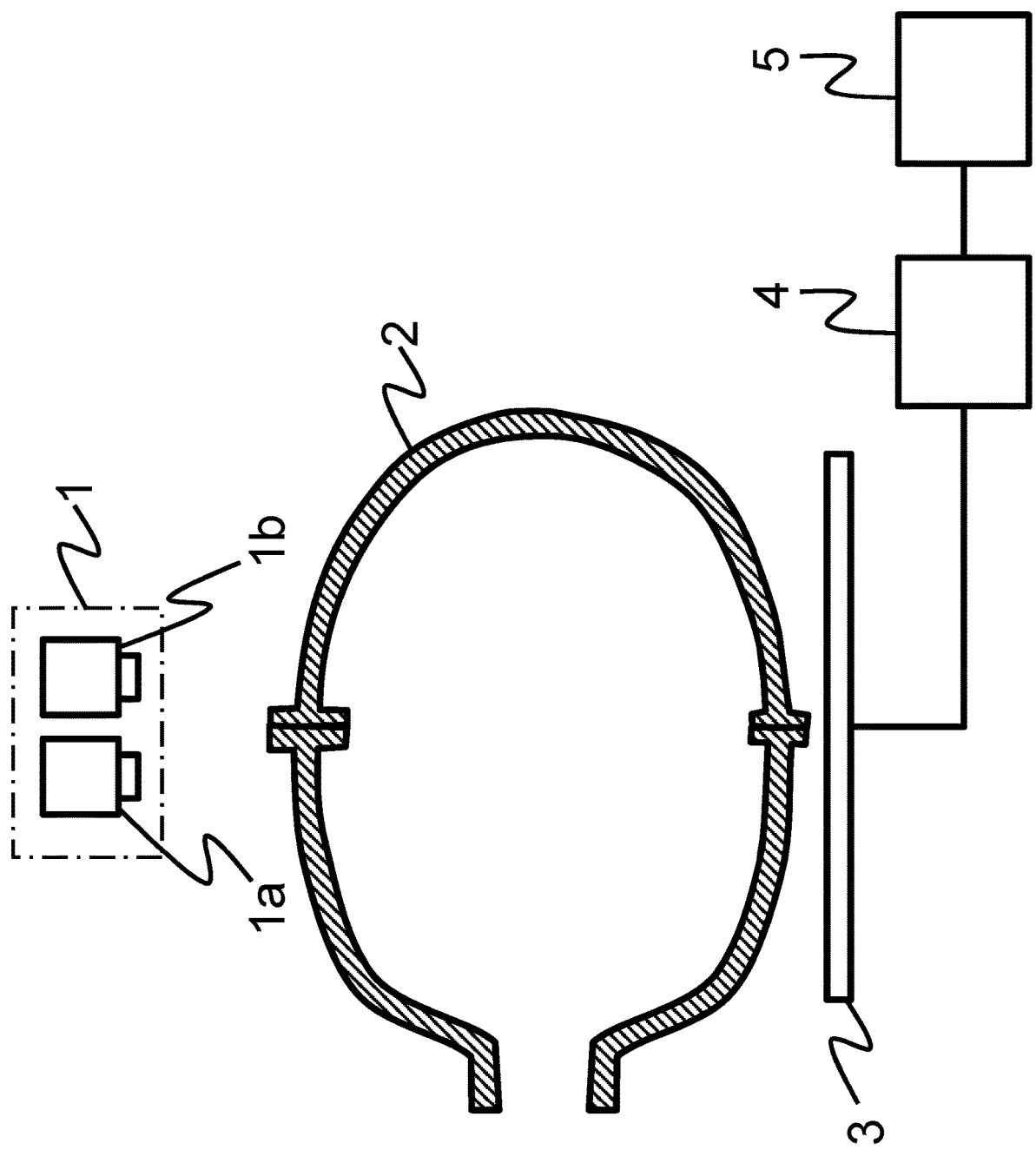
FIG. 1 is a schematic diagram for explaining an embodiment of the present invention.
Figure 2:
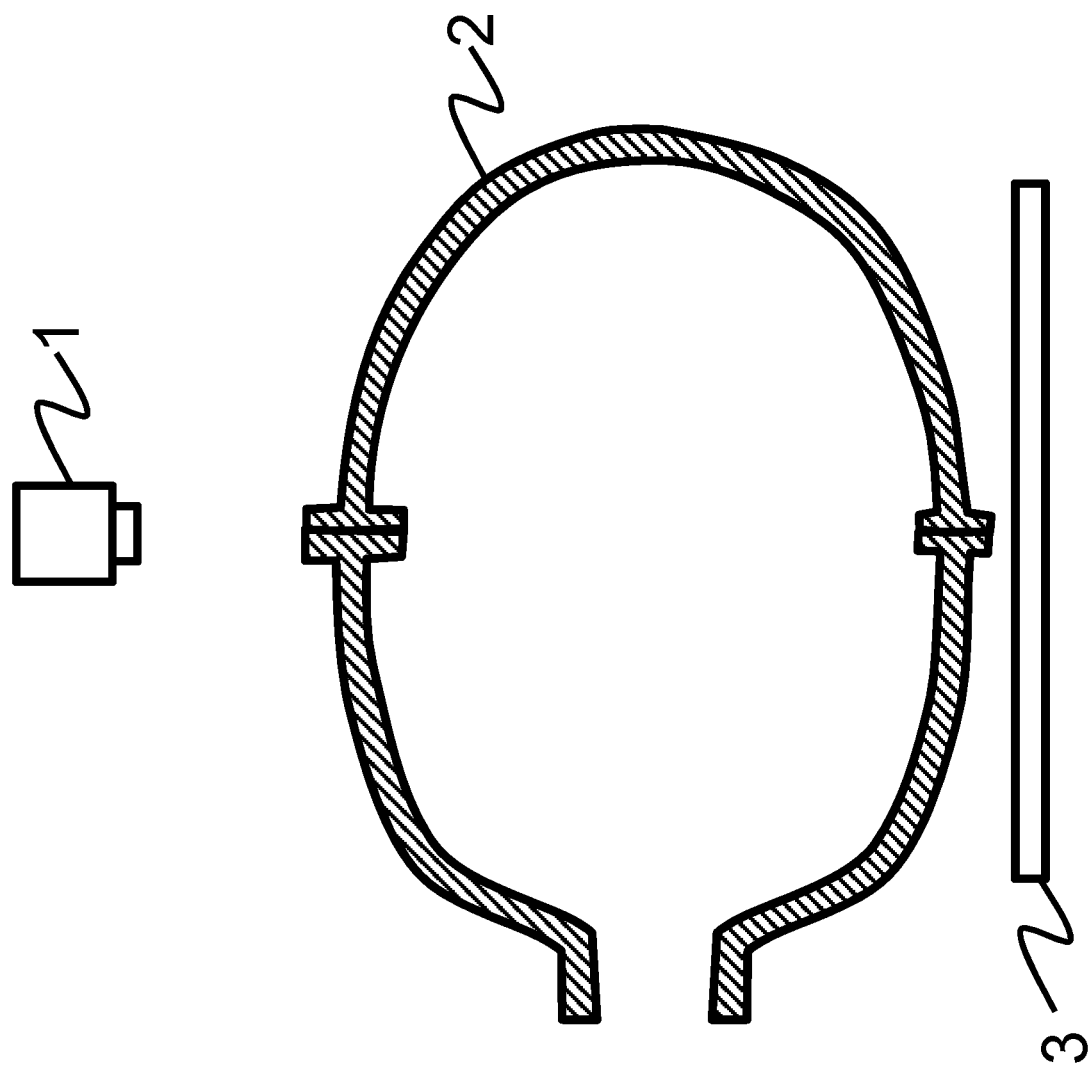
FIG. 2 is a schematic diagram for explaining the inspection setup that incorporates a general type X-ray transmission imaging device.
Figure 3:
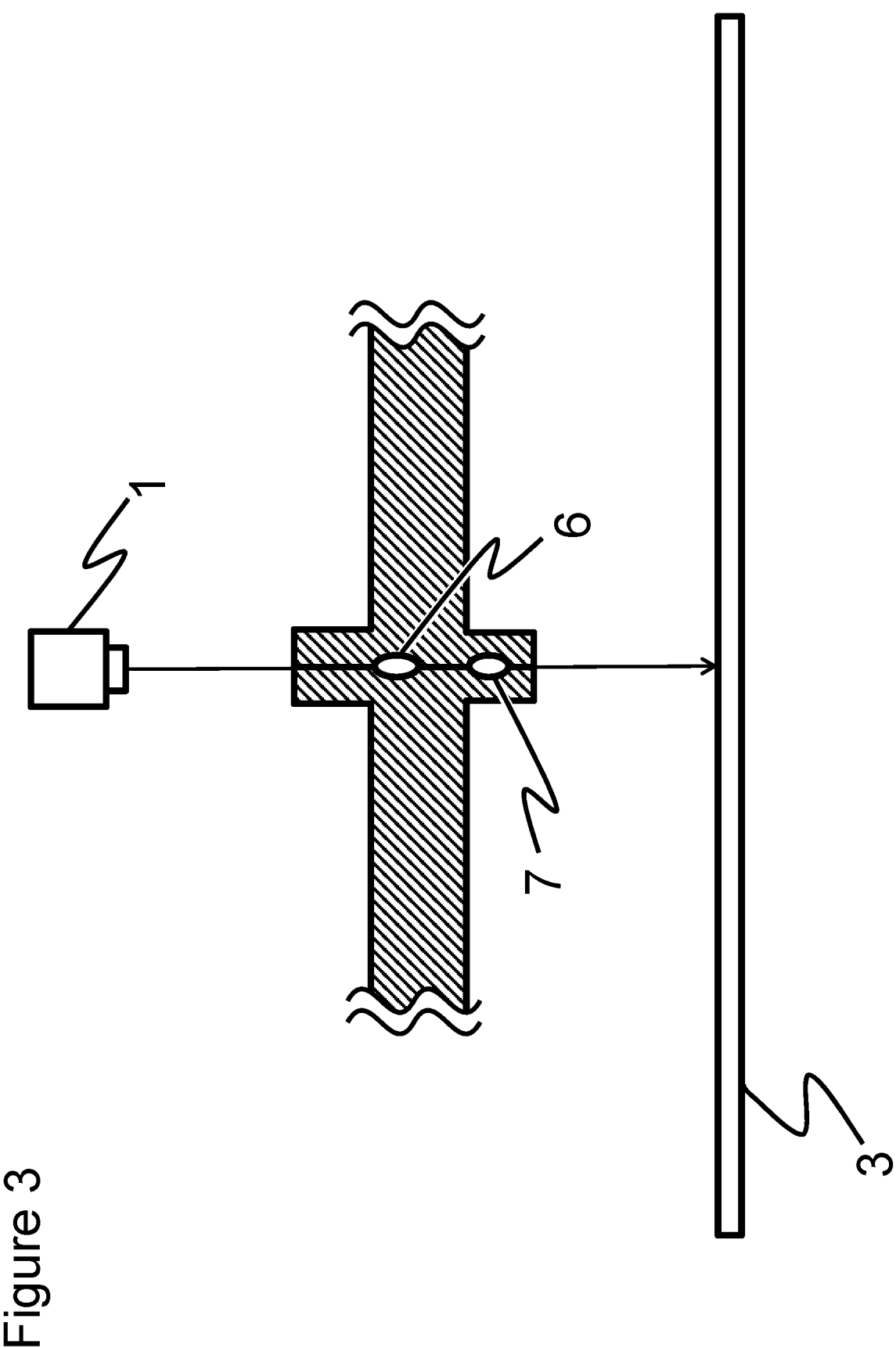
FIG. 3 is a schematic diagram for explaining a typical defect portion and a non-defect portion that cannot be distinguished by an inspection setup incorporating a common X-ray transmission imaging device.

Embodiments in which the inspection apparatus for molded resin articles according to the present invention is applied will be described below with reference to the drawings. It should be understood, however, that the following embodiments only exemplify typical applications of the present invention and the invention is not limited to these embodiments. The procedures described in the following examples may be modified without departing from the spirit of this invention. In addition, the inspection apparatus for molded resin articles according to the present invention can be applied to inspections of various molded resin articles. They include, for example, members of high pressure tanks, resin pipes, and resin structural members. Here, as one example of molded resin article inspection, the inspection of a liner member of a high pressure tank will be described in detail.

First, a molded resin article and a high pressure tank to be inspected according to an embodiment of the present invention will be described. The high pressure tank is a container for filling high pressure gas such as compressed gas and liquefied gas, and in the case where the high pressure gas is hydrogen, for example, such containers include a container to be mounted on a fuel cell vehicle, a container for high pressure hydrogen transport, and a hydrogen station accumulator. There are no specific limitations on the structure of the high pressure tank. To give an example, a high pressure tank includes a liner member to serve as a member of the high pressure tank, one or a plurality of reinforcement layers covering the liner member, and a supply system (valve member, various piping systems, etc.) for supplying high pressure gas to the fuel cell.

There are no specific limitations on the shape of the high pressure tank. By way of example, the high pressure tank may be substantially cylindrical. The high pressure tank has an opening for filling the tank with high pressure gas or extracting the high pressure gas from the tank. The supply system works to close the opening. For the present invention, examples of the molded resin article include members of high pressure tanks such as a liner member and a combination of a liner member provided with a reinforcement layer formed thereon.

Liner Member

A liner member is a member of a tank container that constitutes a part of the housing of the high pressure tank. There are no specific limitations on the shape of the liner member. For example, the liner member has a substantially cylindrical shape and has an accommodation space formed therein. The accommodation space is filled with a high pressure gas. The liner member has an opening as described above. The liner member may be comprised of one member, but is generally comprised of a plurality of divided parts for ease of manufacture. In this case, the plurality of divided parts can be integrated by joining or the like. Methods for producing a liner member include, for example, blow molding and injection molding. On the other hand, the inspection method according to an embodiment of the present invention is suitably used for inspection of the joining surfaces where the plurality of divided parts are joined by injection molding to form a liner member.

There are no specific limitations on the material of the liner member. By way of example, a liner member is made of resin, metal such as aluminum and iron, or the like. In particular, a liner member made of resin that contains voids or impurities in a joint portion tends to easily undergo deformation, breakage, or the like after it is molded into a high pressure tank. However, the inspection method according to an embodiment of the present invention serves appropriately to detect such voids and impurities as described later. Therefore, the inspection method according to an embodiment of the present invention is particularly suitable for liner members made of resin. Resins are so high in X-ray absorptivity that it is preferable for the liner member to contain at least one selected from the group consisting of polyolefin resins, ethylene-vinyl alcohol copolymers, and polyamide resins because impurities or the like in the liner member can be detected with higher accuracy by an X-ray detector which will be described later.

It is more preferable that the liner member contains a polyamide resin. Since the polyamide resin has a high X-ray absorptivity, voids, resin impurities, and the like in the polyamide resin can be detected easily. In particular, in the case where the high pressure gas is hydrogen gas, the hydrogen gas has a low molecular weight and therefore easily dissolves in the liner member. As a result, the high pressure tank for hydrogen gas is liable to be deformed or destroyed in the joint portion even when a slight gap or impurity exists in the joint portion of the liner member. The inspection method according to an embodiment of the present invention described later serves for easy detection of such voids, resin impurities, and the like. Therefore, the inspection method according to an embodiment of the present invention works suitably for accurate detection and appropriate identification of impurities and the like when the liner member is of a polyamide resin.

Reinforcement Layer

It is preferable for the outer surface of the liner member to be covered by one or more reinforcement layers to reinforce the liner member. There are no specific limitations on the material of the reinforcement layers. By way of example, the reinforcement layer is a fiber reinforced resin layer. Examples of the fiber reinforced resin used to form the fiber reinforced resin layer include, for example, carbon fiber reinforced plastic (CFRP) and glass fiber reinforced plastic. Some of these fiber reinforced resins may be used in combination. The liner member may also be covered by two reinforcement layers made of different fiber reinforced resins. When the fiber reinforced resin is, for example, a carbon fiber reinforced plastic, the fiber reinforced resin layer is mainly composed of reinforcing fiber, such as carbon fiber reinforced plastic used to be wound around the outer surface of the liner member, and a thermosetting resin used to bind reinforcing fibers to each other.

Here, the description returns to the inspection method. The inspection method according to the present invention is preferably performed to inspect the joining surface of the liner member of a high pressure tank before a reinforcement layer is added. Specifically, in the inspection method, X-ray is emitted from an X-ray emitting apparatus towards the liner member, and the X-ray beam that have passed through the liner member is detected using an X-ray detector, thereby determining whether the liner member is an acceptable one or an unacceptable one.

FIG. 1 is a schematic diagram for explaining the inspection apparatus according to an embodiment of the present invention. The X-ray emission means 1 is a device for emitting X-ray towards the molded resin article 2. There are no specific limitations on the shape and dimensions of the X-ray emitting apparatus. The X-ray emission means 1 may be provided with a power supply cable (not shown) for driving the X-ray emitting apparatus. In this case, it is preferable that the power supply cable and the like have a shape and dimensions that do not interfere with the molded resin article 2. The emitted X-ray beams need to reach the molded resin article through a plurality of paths. For an embodiment of the present invention, X-ray beams are emitted by two X-ray emission means, namely, X-ray emission means 1a and X-ray emission means 1b. The emitted X-ray beams pass through the molded resin article near the X-ray emission means and the molded resin article near the X-ray detection means, and are detected by the X-ray detection means 3. Although the arrangement of the X-ray emission means 1 is not particularly defined, it is preferable that at least one of the plurality of X-ray emission means is located so as to prevent both the joining interface near the X-ray emission means and the joining interface near the X-ray detection means from being in a transmission path. Here, the X-ray emission means 1a and the X-ray emission means 1b are arranged side by side so as to be disposed on either side of the molded resin articles, and both of them are located so that neither of the joining interface near the X-ray emission means nor the joining interface near the X-ray detection means are in the irradiation paths.

The molded resin article 2 is illustrated to represent a high pressure tank member composed of two divided molded members joined together in a cylindrical shape.

The X-ray detection means 3 is a device for detecting the X-ray beams that have passed through the molded resin article 2. The X-ray detection means has at least one X-ray detector and there may exists one X-ray detection means to detect X-ray beams emitted from a plurality of X-ray emission means 1 wherein the plurality of X-ray emission means emit X-ray beams at different timings, or a plurality of X-ray detection means arranged in combination with a plurality of X-ray emission means 1 to perform simultaneous detection of the X-ray beams, or one X-ray detection means in combination with a plurality of X-ray emission means 1 wherein the X-ray detection means move to different positions where the X-ray beams can be detected. Generally, in the case of voids, X-ray beams are detected more strongly than the surroundings because they are easy to penetrate, whereas in the case of impurities, they are detected either strongly or weakly depending on the relationship between the specific gravity of the impurities and the specific gravity of the resin material constituting the molded resin article. In addition, since a burr portion has a thickness larger than that of the normal portion of the molded resin article, its image is observed weakly as a whole. The reference marker 8 serves as a reference for accurate identification of the surface height position of the molded resin article 2 and allows the X-ray detection means to perform accurate detection and therefore, it is preferably made of a metallic material that is less permeable to X-ray than the molded resin article, which is made of resin. Furthermore, since the reference marker 8 is used for accurate identification of the surface height position of the molded resin article 2, a plurality of reference markers 8 may be arranged so that they are detected by the X-ray detection means 3. In addition, other means of identifying the surface height of the molded resin article with high accuracy include the use of a mechanism (not shown) that works for mechanical positioning to fix the molded resin article with high accuracy, thereby setting a predetermined reference height position without using the reference marker 8 or the like. Alternatively, a measuring means (not shown) that can measure the height position of the fixed molded resin article with high accuracy may be used to perform sequential measurement of the reference height position. Examples of the measuring means include laser triangulation type displacement meter, laser interferometer, ultrasonic range finder, eddy current type displacement sensor, and stylus type displacement meter, of which the laser triangulation type displacement meter is preferred from the viewpoint of non-contact measurement, little influence by the material of the measuring object, response speed, and the like. In this description of the embodiment of the present invention, it is assumed that one reference marker 8 is disposed at a position that falls within the detection range of the X-ray detection means 3.

Here, the X-ray detection means 3 may be a general purpose type X-ray detector. As an example, the X-ray detection means 3 may be a direct conversion type X-ray detector or an indirect conversion type X-ray detector. More specifically, the X-ray detection means 3 may be an X-ray film, image intensifier, computed radiography (CR), flat panel detector (FPD), or the like.

With respect to the arrangement of the X-ray detecting elements of the X-ray detection means 3, detecting elements may be arranged two-dimensionally to form an area sensor type X-ray detector or detecting elements may be arranged one-dimensionally to form a line sensor type X-ray detector. Depending on which detection method is used, the method for sequentially changing the inspection range may be optimized. When an area sensor system is adopted, it is provided with at least a mechanism for sequentially switching the field of view in accordance with the inspection field of view of the area sensor, whereas when a line sensor system is adopted, it is provided with at least a mechanism for continuously moving the inspection field of view.

Here, the X-ray detection means 3 is preferably an indirect conversion type FPD in view of the fact that a development process or the like is unnecessary and accordingly the time required for inspection can be shortened as compared, for example, with the case where an X-ray film is used.

There are no restrictions in terms of usable temperature or the like on indirect conversion type FPDs as compared with direct conversion type detectors. Therefore, indirect conversion type X-ray detectors are high in handleability. Furthermore, it is preferable to use an indirect conversion type FPD having a cell scintillator. In an indirect conversion type FPD, a scintillator panel is used to convert radiation into visible light. The scintillator panel contains an X-ray phosphor such as cesium iodide (CsI), and the X-ray phosphor emits visible light after receiving emitted X-ray. Then the light is converted into electric signals by a TFT (thin film transistor), CCD (charge-coupled apparatus), and the like, thereby converting the X-ray information into digital image information. However, as the X-ray phosphor emits light in an indirect conversion type FPD, the visible light may be scattered by the phosphor itself, easily leading to images with decreased sharpness. On the other hand, in an FPD provided with a cell type scintillator, the cells partitioned by partition walls are filled with a phosphor, and the influence of light scattering can be suppressed. As a result, the FPD provided with a cell type scintillator is so high in sharpness that impurities and voids in the molded resin article 2 can be detected with high sensitivity.

The X-ray detection means 3 used in the inspection method according to the present invention is more preferably a cell type scintillator produced by processing partition walls containing glass as main component by photolithography using a photosensitive paste containing glass powder because this permits easily formation of a cell type scintillator having a large area and a high sharpness. There are no specific restrictions on the pixel size of the sensor in the X-ray detection means 3. By way of example, the pixel size of the sensor is preferably 20 to 300 μm. When the pixel size is less than 20 μm, minute impurities that do not contribute to deformation or destruction of the molded resin article 2 are detected, and acceptable articles tend to be erroneously judged to be unacceptable. In addition, in the case of such a pixel size, image data will be very large, and the time required for signal reading and image processing will tend to be long. On the other hand, when the pixel size exceeds 300 μm, there is a possibility that impurities and the like cannot be sufficiently detected.

The image processing means 4 is connected to the X-ray detection means 3 and includes a height position calculation means for calculating the height position of a defect candidate from a plurality of X-ray detection images acquired by the X-ray detection means 3, and a selection means 5 for judging the state of the defects candidate from the height position.

Figure 6:
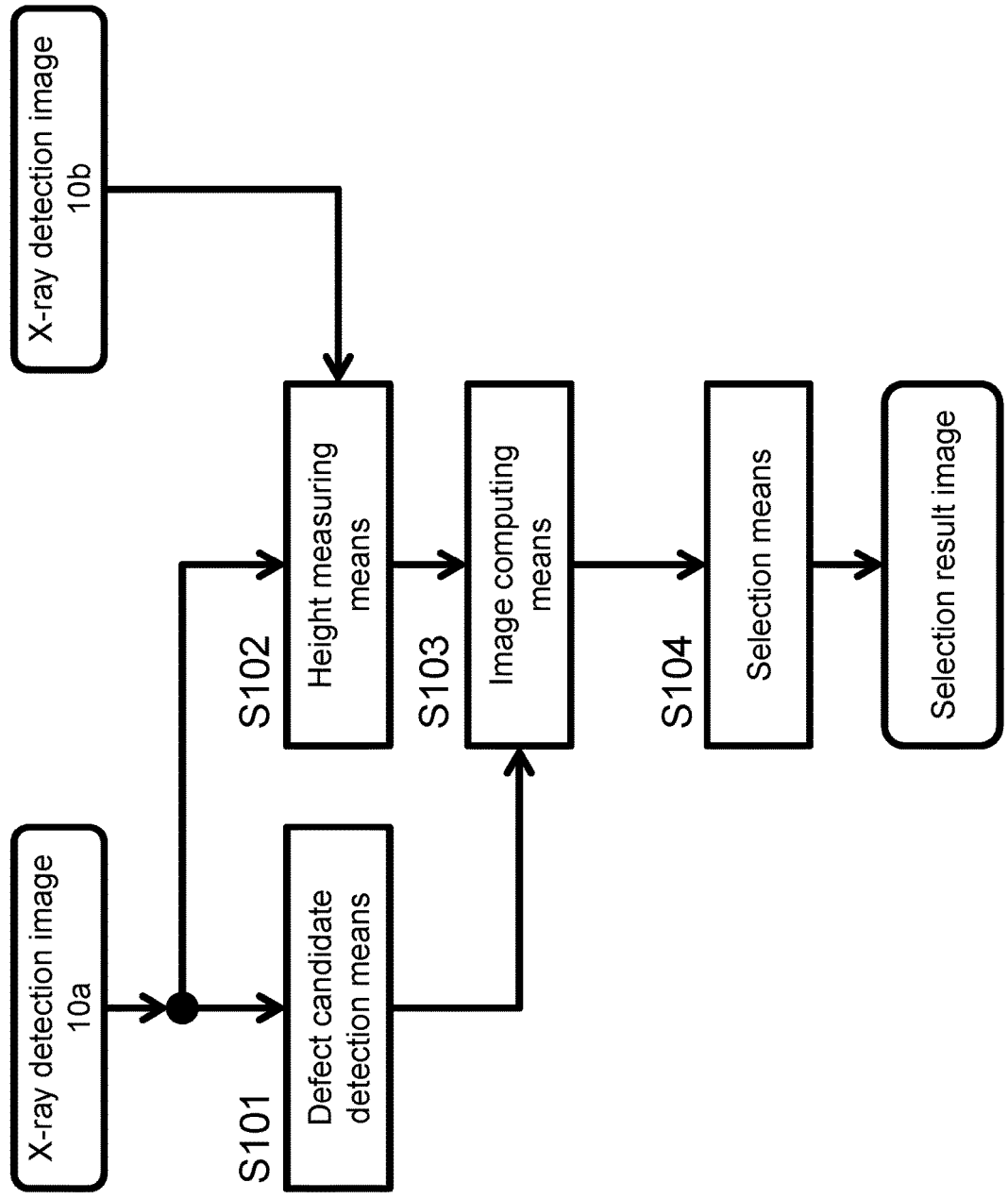
FIG. 6 is a flow chart for explaining the processing procedure performed by the image processing means.

The flow of processing by the image processing means 4 will be described with reference to FIG. 6. FIG. 6 is a flow chart for explaining the processing procedure performed by the image processing means. The X-ray detection image 10*a* is a detection image produced from the X-ray beams emitted from the X-ray emission means 1*a* and detected by the X-ray detection means 3, and the X-ray detection image 10*b* is a detection image produced from the X-ray beams emitted from the X-ray emission means 1*b* and detected by the X-ray detection means 3. In a detection image, as the intensity of detected X-ray beams is output as a luminance value, the luminance value is large (bright) in a portion where X-ray beams are strongly detected whereas the luminance value is small (dark) in a portion where X-ray beams are weakly detected.

Figure 7:
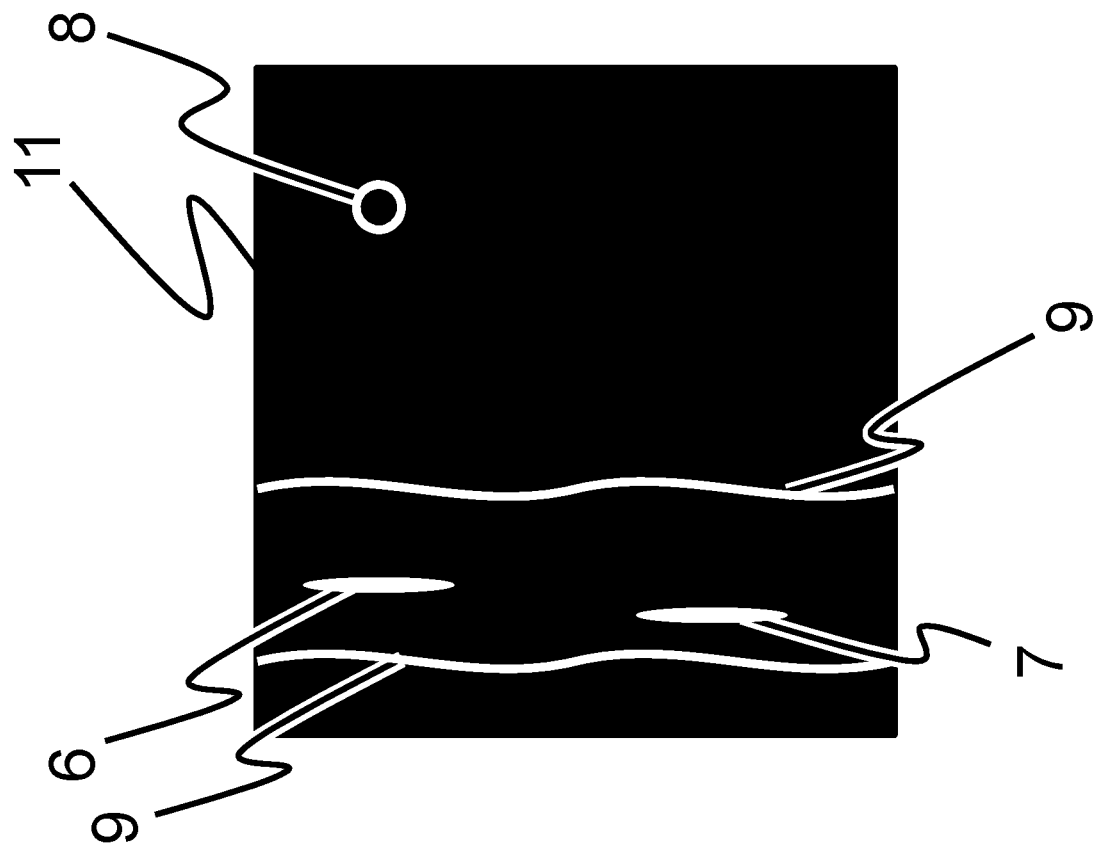
FIG. 7 is a typical processed image acquired by the defect candidate detection means.
Figure 8:
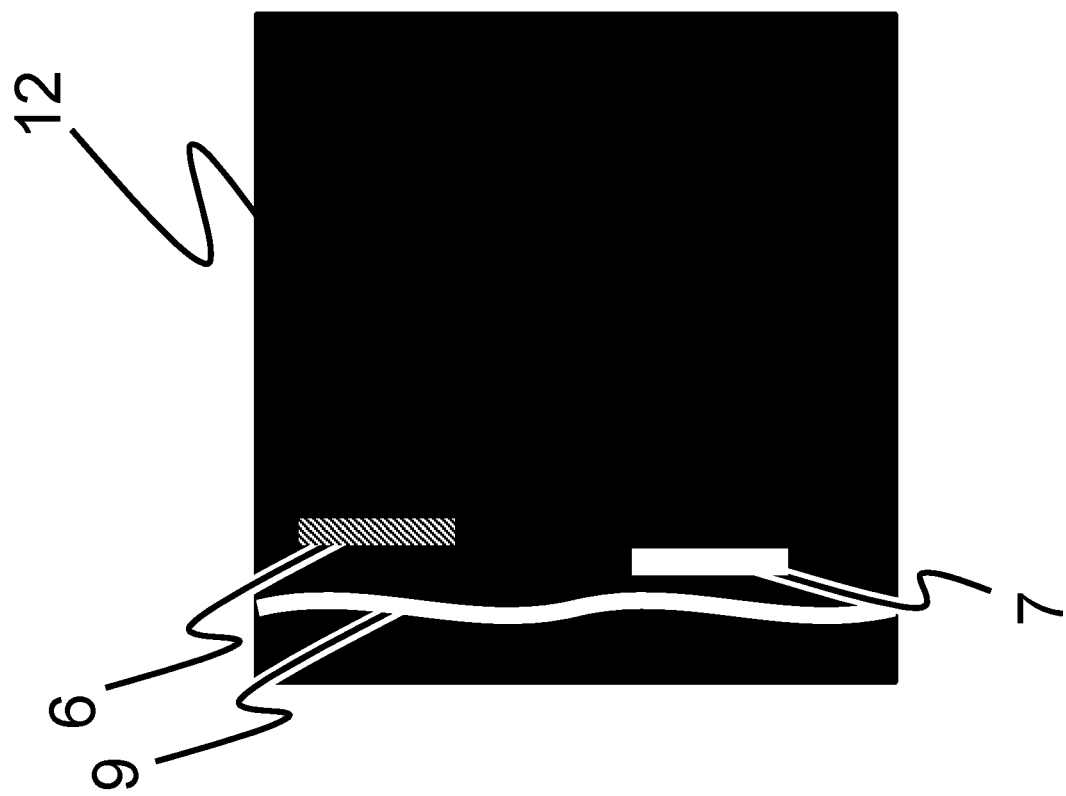
FIG. 8 is a typical result of stereo matching processing.
Figure 9:
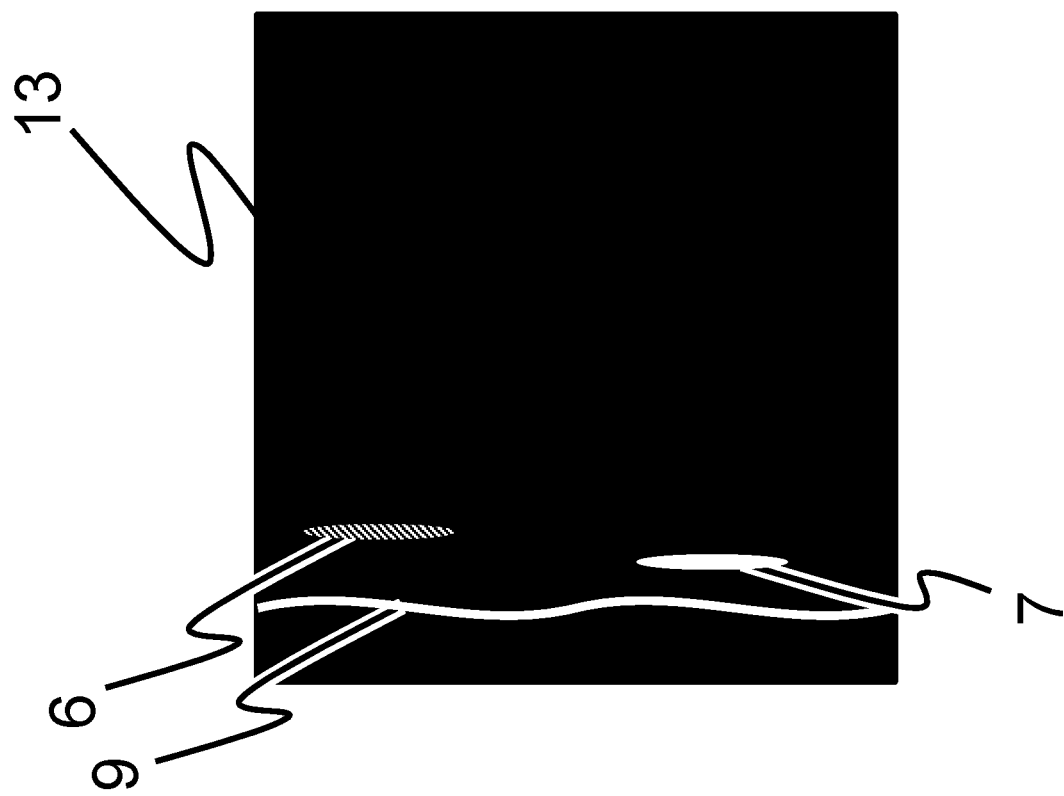
FIG. 9 is a typical image resulting from height position calculation.
Figure 10:
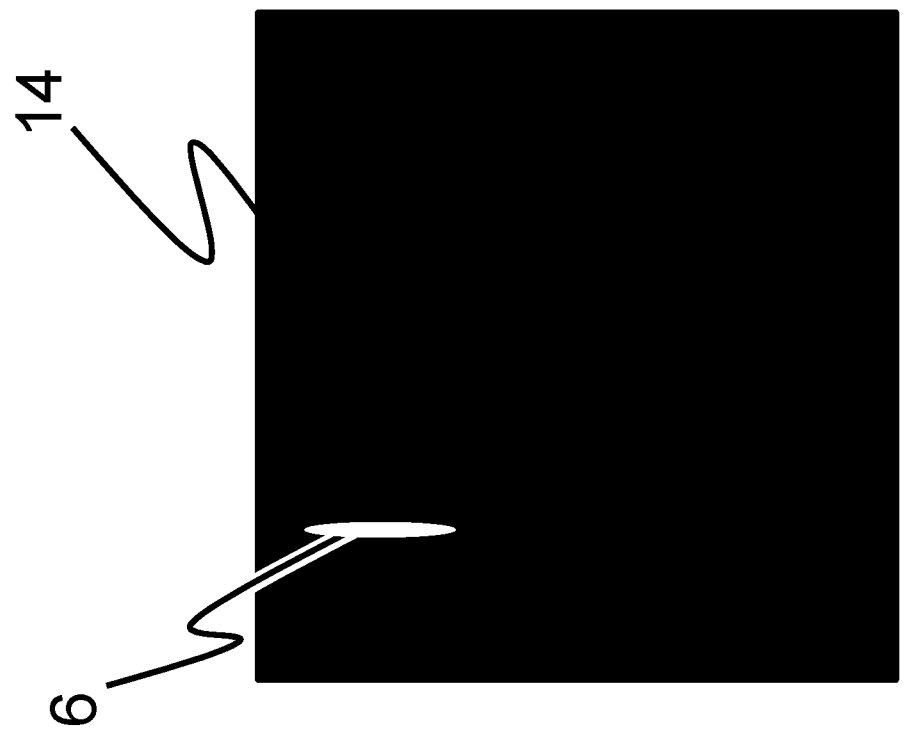
FIG. 10 is a typical selection result acquired by the selection means.

S101 represents the defect candidate detection means for detecting a defect candidate region in an X-ray detection image, which detects, as a defect candidate, an area region that is defined by the luminance threshold in the bright direction and the luminance threshold in the dark direction to serve for separating defect candidate and non-defect regions in an X-ray detection image which is entered as two-dimensional image data. The detection procedure is performed on at least one X-ray detection image of the plurality of X-ray detection images, and in the Examples of the present invention, it is performed on the X-ray detection image 10*a* that is obtained from X-ray beams detected after being emitted from the X-ray emission means 1*a*. In the detection of defect candidates, those regions satisfying the thresholds may be narrowed down based on the size of the detected area or may be narrowed down based on feature values of the detected shape. For example, since voids, impurity components, or the like that act as defects generally have elongated shapes aligned in nearly the same directions along the joining interface, the direction (angle) of the detected shape and the thinness (aspect ratio) thereof may be used as feature values for narrowing down them. In addition, since the thickness increases above and below a defect portion due to the influence of burrs generated at the time of joining and accordingly the periphery of the defect is detected as a dark portion, a spatial filter or the like may be applied prior to the detection based on luminance thresholds. For example, to suppress the influence of a dark portion attributed to a burr, a high-pass filter for cutting low frequency components in the X-ray detection image is effective, but in the present case, as seen in the defect candidate image shown in FIG. 7, an erroneous detection region 9 is identified as a defect candidate even along the boundary line between the burr portion and the normal high pressure tank member portion where the luminance in the X-ray detection image abruptly changes.

Figure 4:
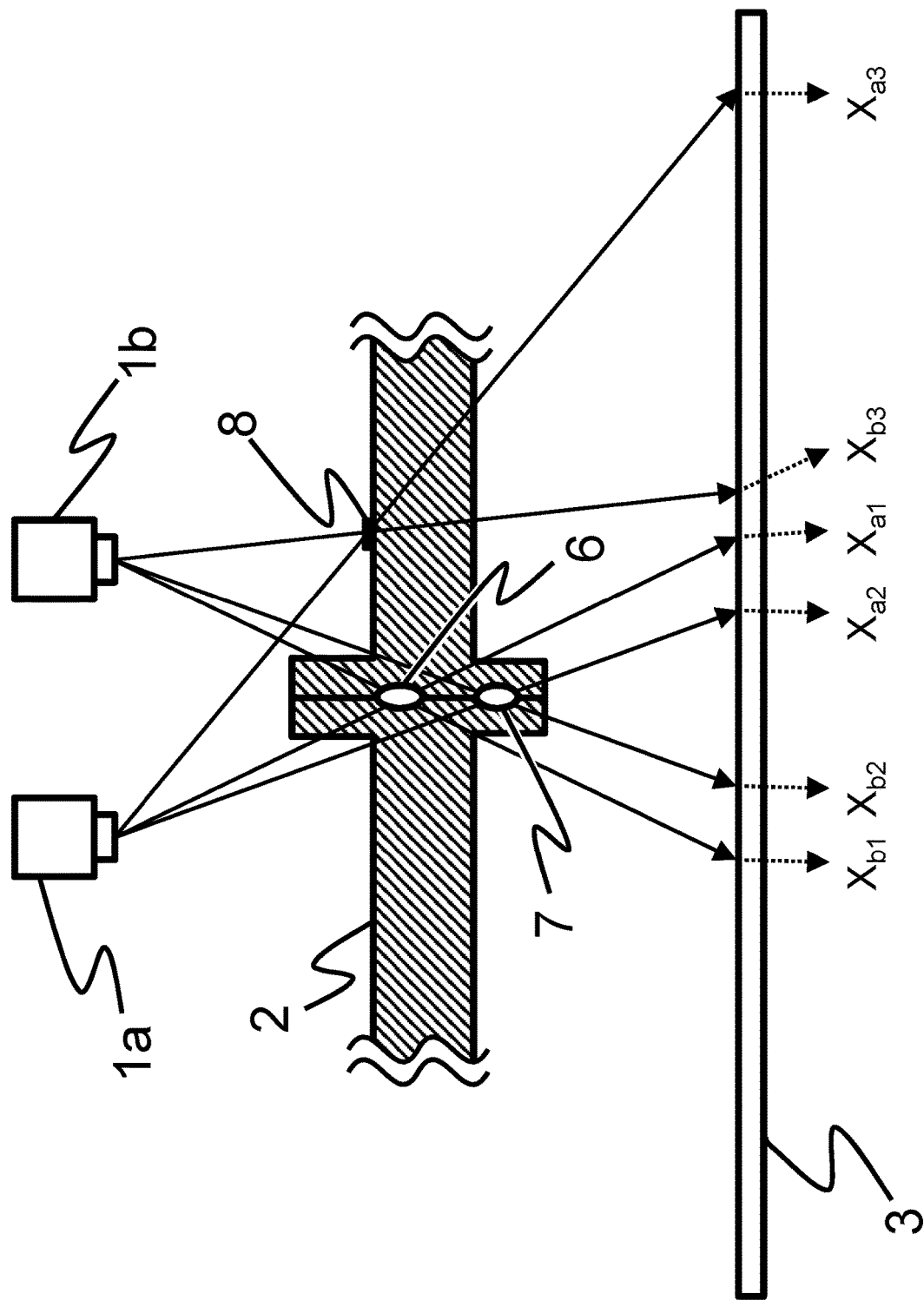
FIG. 4 is a schematic diagram for explaining the difference between the position of a defect portion and that of a non-defect portion detected by the X-ray detection means in the case where X-ray beams are emitted through a plurality of paths.
Figure 5:
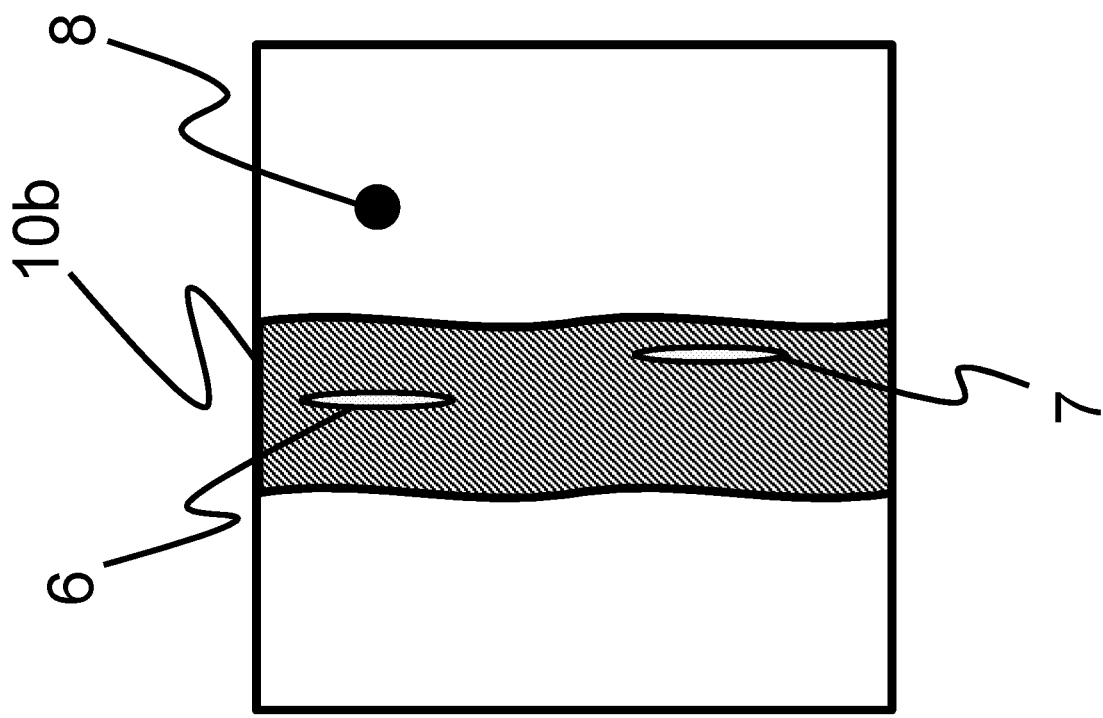
FIG. 5 is a typical image acquired by the X-ray detection means.
Figure 5:
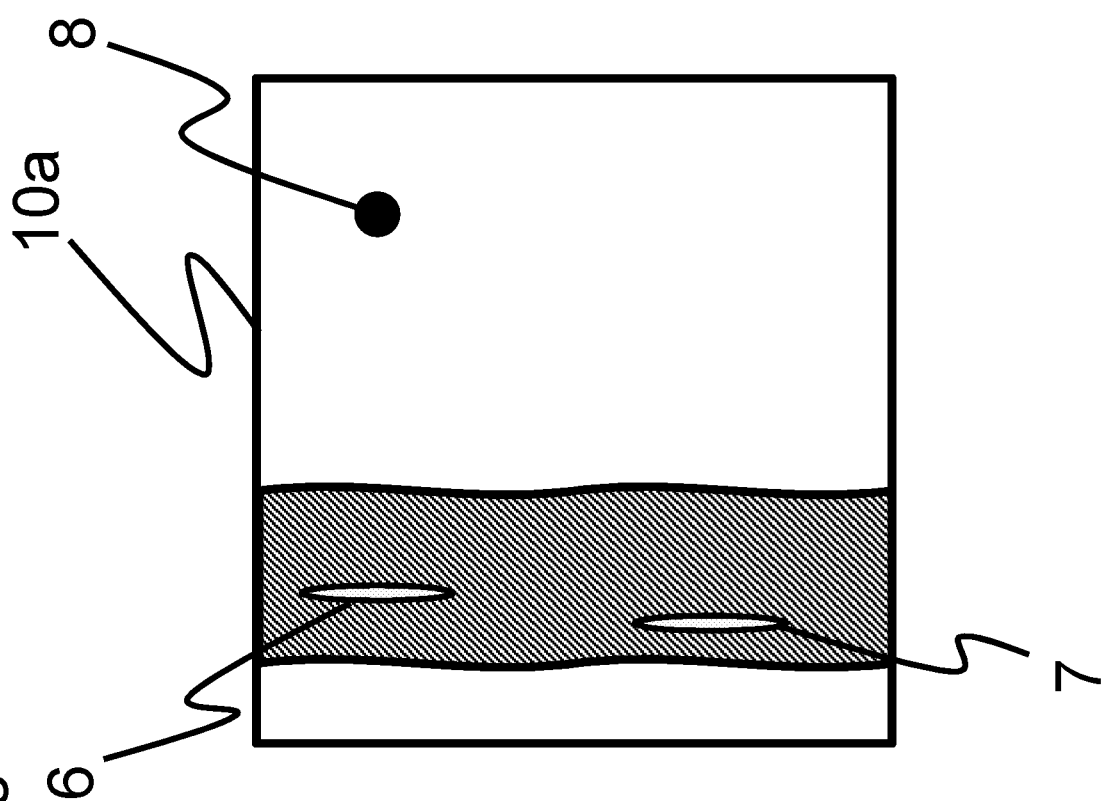

The S102 represents a height measuring means for measuring the height of the same point detected in a plurality of X-ray detected images. In order to deepen the understanding of the principle of this height measurement, it will be described in detail with reference to FIGS. 4 and 5. FIG. 4 is a schematic diagram for explaining the difference between the position of a defect portion and that of a non-defect portion detected by the X-ray detection means in the case where X-ray beams are emitted through a plurality of paths. To simplify the description, this shows only the cross section of a part of the joint portion of the molded resin article 2 located nearer to the X-ray emission means 1. In the case where there exist a joint portion void defect 6 in the joint portion of the molded resin article 2, a burr void 7 in the burr portion, and a reference marker 8 on the surface of the molded resin article 2, the X-ray beams emitted from the X-ray emission means 1*a* detects the joint portion void defect 6 at the coordinate position of Xa1, the burr void 7 at the coordinate position of Xa2, and the reference marker 8 at the coordinate position of Xa3 on the X-ray detector 3, resulting in such an image as the X-ray detecting image 10*a* shown in FIG. 5. The X-ray beams emitted from the X-ray emission means 1*b* detects the joint portion void defect 6 at the coordinate position of Xb1, the burr void 7 at the coordinate position of Xb2, and the reference marker 8 at the coordinate position of Xb3 on the X-ray detector 3, resulting in such an image as the X-ray detecting image 10*b* shown in FIG. 5. Here, the height position Hd0 of the joint portion void defect 6 is calculated as Equation 1, wherein f is the distance from the X-ray emission means 1*a* and the X-ray emission means 1*b* and w is the distance between the X-ray emission means 1*a* and the X-ray emission means 1*b*.

$$Hd0 = f \times w / (|Xa1 - Xb1|) \quad \text{(Equation 1)}$$

The height position Hf0 of the burr void 7 is calculated as Equation 2.

$$Hf0 = f \times w / (|Xa2 - Xb2|) \quad \text{(Equation 2)}$$

The height positions Hd and Hf indicate the distances from the X-ray emission means, but it is necessary to provide, as height position information, the height difference with respect to the surface position of the molded resin article 2, and therefore, in this example, it is calculated as Equation 3 assuming that the height position of the reference marker 8 represents the surface position Hm0 of the molded resin article 2.

$$Hm0 = f \times w / (|Xa3 - Xb3|) \quad \text{(Equation 3)}$$

Although, as described above, the height position of the reference marker 8 may be used as the surface position Hm0 of the molded resin article 2, if as described above, a mechanism that works for mechanical positioning to fix the molded resin article with high accuracy is available, a predetermined reference height position may be set without using a device similar to the reference marker 8. Alternatively, a measuring means that can measure the height position of the fixed molded resin member of a high pressure tank with high accuracy may be used to perform sequential measurement of the reference height position. Examples of the measuring means include laser triangulation type displacement meter, laser interferometer, ultrasonic range finder, eddy current type displacement sensor, and stylus type displacement meter, of which the laser triangulation type displacement meter is preferred from the viewpoint of non-contact measurement, little influence by the material of the measuring object, response speed, and the like.

As a result, the height position Hd1 of the joint portion void defect 6, which is a defect, from the surface of the molded resin article can be determined as Equation 4.

$$Hd1 = Hd0 - Hm0 \quad \text{(Equation 4)}$$

Similarly, the height position Hf1 of the burr void 7, which is not a defect, from the surface of the molded resin article can be determined as Equation 5.

$$Hf1 = Hf0 - Hm0 \quad \text{(Equation 5)}$$

In order to sequentially execute the height measurement process, this embodiment of the present invention uses a technique called stereo matching for its execution. This technique is also called block matching, which is a widely adopted method that uses images recorded from a plurality of different viewpoints and calculates height position information from a difference (parallax) in the observed position of the same point among the recorded images, and although detailed description of the method is omitted here, but in this method, an image block of a predetermined two-dimensional size centered on a pixel of interest is first set in one image and a position in another image where the similarity between the former image and the latter image is highest is identified by an image similarity calculation method such as normalized correlation, followed by performing sequential calculation of height information from the coordinate position information of the two images linking the position. With respect to the height information calculated by this method, the height of the part corresponding to the reference marker 8 is determined as Hm0, and Hm0 is subtracted from the entire area of the image for which the parallax is calculated above, which indicate that a position located higher than the reference marker 8, that is, nearer to the X-ray detection means 3 than the surface containing the reference marker 8 in the molded resin article 2 gives height information having a positive value whereas a position located lower than the reference marker 8, that is, nearer to the X-ray emission means 1 than the surface containing the reference marker 8 in the molded resin article 2 gives height information having a negative value. Accordingly, a stereo-matching image 12 is obtained by reading out only the information on a height area having a positive value, which represents the direction of the area to be examined. In the present example, a portion corresponding to the reference marker 8 has a height of zero in the stereo-matching image 12, whereas a height is outputted in a part of the block region including the joint portion void defect 6, the burr void 7, and the erroneous detection region 9 corresponding to the abrupt change in luminance in the X-ray detection image 1*a*. When performing height measurement by the stereo matching method, preprocessing may be performed on the X-ray detection image 10*a* and the X-ray detection image 10*b* so that a region regarded as a defect candidate can be detected more easily. For example, those regions satisfying the predetermined threshold in the light direction or the dark direction may be narrowed down based on the size of the detected area or may be narrowed down based on feature values of the detected shape. For example, since voids and impurity components that act as defects generally have elongated shapes aligned in nearly the same directions along the joining interface, the direction (angle) of the detected shape and the thinness (aspect ratio) thereof may be used as feature values for narrowing down them. In addition, since the thickness increases above and below a defect portion due to the influence of burrs generated at the time of joining and accordingly the periphery of the defect is detected as a dark portion, a spatial filter or the like may be applied prior to the detection based on luminance thresholds. For example, to suppress the influence of a dark portion attributed to a burr, a high-pass filter for cutting low frequency components in the X-ray detection image is effective.

The S103 represents an image computing means. A height position calculation image 13 of a defect candidate is obtained by performing logical multiplication of the defect candidate image 11 generated by the defect candidate detection means (S101) and the stereo matching image 12 generated by the height measuring means (S102).

The S104 represents a selection means. Reference numeral 5 in FIGS. 1 and 11 to 14 denotes the selection means (S104) which is part of the image processing means 4. For the height position calculation image 13 of a defect candidate calculated by the image computing means (S103), the selection means (S104) determines whether or not the defect candidate is a defect from the measured height information of the defect candidate. Specifically, a upper height limit value and a lower height limit value are set first as predetermined height thresholds, and a defect candidate having a measured height value falling within the range between the thresholds is judged to be a defect generated in the joint portion whereas a defect candidate having a measured height value falling within the range between the thresholds is judged to be a void or impurity component existing in a burr located above or below the joint portion, or an erroneous detection. An upper limit value and a lower limit value based on the thickness design values of the joint portion of the molded resin article are preferably used as the thresholds values.

The selection means (S104) may include a distance setting means for setting the distance from the X-ray emission means 1 to the molded resin article 2, an inspection range setting means for setting the inspection range based on the distance and the thickness of the molded resin article, and a defect determination means for defect determination when the inspection range includes a defect candidate.

The distance setting means sets the distance Hm0 from the X-ray emission means 1 to the surface of the molded resin article 2. The distance may be set by any of the following: using a mechanism that works for highly accurate mechanical positioning to fix the surface of the molded resin article 2 at Hm0, using a measured distance between the X-ray emission means 1 and the molded resin article as Hm0, using the height of the reference marker 8 calculated by the stereo matching method described above as Hm0, or using a value measured by a measuring apparatus such as laser triangulation displacement meter, laser interferometer, ultrasonic range meter, eddy current displacement sensor, or stylus type displacement sensor as Hm0. Measurement by a laser triangulation displacement meter is preferred from the viewpoint of non-contact measurement, little influence by the material of the measuring object, response speed, and the like. More specifically, furthermore, the distance setting means may include a distance input means for inputting a target distance value from the X-ray emission means 1 to the molded resin article 2, a distance measuring means for measuring the distance from the X-ray emission means 1 to the molded resin article 2, and a distance correction means for calculating the difference between the input value entered by the distance input means and the measured value taken by the distance measuring means and making a correction based thereon so that the distance becomes equal to the input value.

In this case, for example, the distance input means inputs the target distance from the X-ray emission means 1 to the molded resin article 2 as Hm0 so that the photographing magnification becomes constant. The distance measuring means, which is designed to measure the distance between the X-ray emission means 1 and the molded resin article 2, may use, as a measured value, the height of the reference marker 8 calculated by the stereo matching method described above or the value measured by a measuring apparatus such as laser triangulation displacement meter, laser interferometer, ultrasonic range meter, eddy current displacement sensor, or stylus type displacement sensor. Measurement by a laser triangulation displacement meter is preferred from the viewpoint of non-contact measurement, little influence by the material of the measuring object, response speed, and the like.

The distance correction means calculates the difference between the input value entered by the distance input means and the measured value taken by the distance measuring means and making a correction based thereon so that the distance becomes equal to the input value, which may be achieved by moving the molded resin article 2 using a uniaxial moving mechanism that moves in the direction parallel to the optical axis that connects the X-ray emission means 1 and the X-ray detection means 3 via the shortest distance.

The inspection range setting means obtains the upper limit value and the lower limit value of the inspection range from the wall thickness design value of the joint portion and use them for setting. Specifically, the lower limit value is set on the basis of an allowable depth from the surface of the molded resin article 2 that is tolerable even if a defect occurs, and the upper limit value is set on the basis of the wall thickness design value of the molded resin article 2 and the allowable depth that is tolerable even if a defect occurs. Here, in order to prevent a defect from being overlooked, the upper limit value and the lower limit value may be adjusted so that the inspection range is broadened as compared with the wall thickness design value. According to preferred practice, the threshold value may be narrowed for the upper limit value whereas the threshold value may be widened for the lower limit value.

The defect determination means determines whether or not the height position of a defect candidate calculated by the equation 4 or 5 given above is included in the range between the upper limit and the lower limit value that are determined by the inspection range setting means described above. Since the height of a defect is not a specific value, but may have a certain height range depending on the shape, a defect candidate is judged to be a defect if a part thereof is included in the above-mentioned range between the upper limit and lower limit of the inspection range. However, when the area of the defect is small or when the gradient of the height of the defect is steep, the height information of the defect may not include values that represent the upper limit and lower limit of a range in some cases, and accordingly, the defect candidate may be judged as a defect if the maximum height of the defect is lower than the upper limit while the minimum height is lower than the lower limit, thereby permitting defect determination in the above cases.

In this embodiment of the present invention, the erroneous detection region 9 and the void 6 in the burr are located below the predetermined upper height limit value and therefore were not judged to be defects, and only the void defect 5 in the joint portion was located in the range between the upper height limit and the lower height limit and judged to be a defect and gave a defect selection result image 14.

Thus, an embodiment of the present invention has been described above with reference to drawings, taking as an example a setup in which a plurality of X-ray emission means 1 are used to provide a plurality of X-ray emitting paths. For an embodiment of the present invention, such a modified embodiment as described below, for example, can be adopted.

Figure 11:
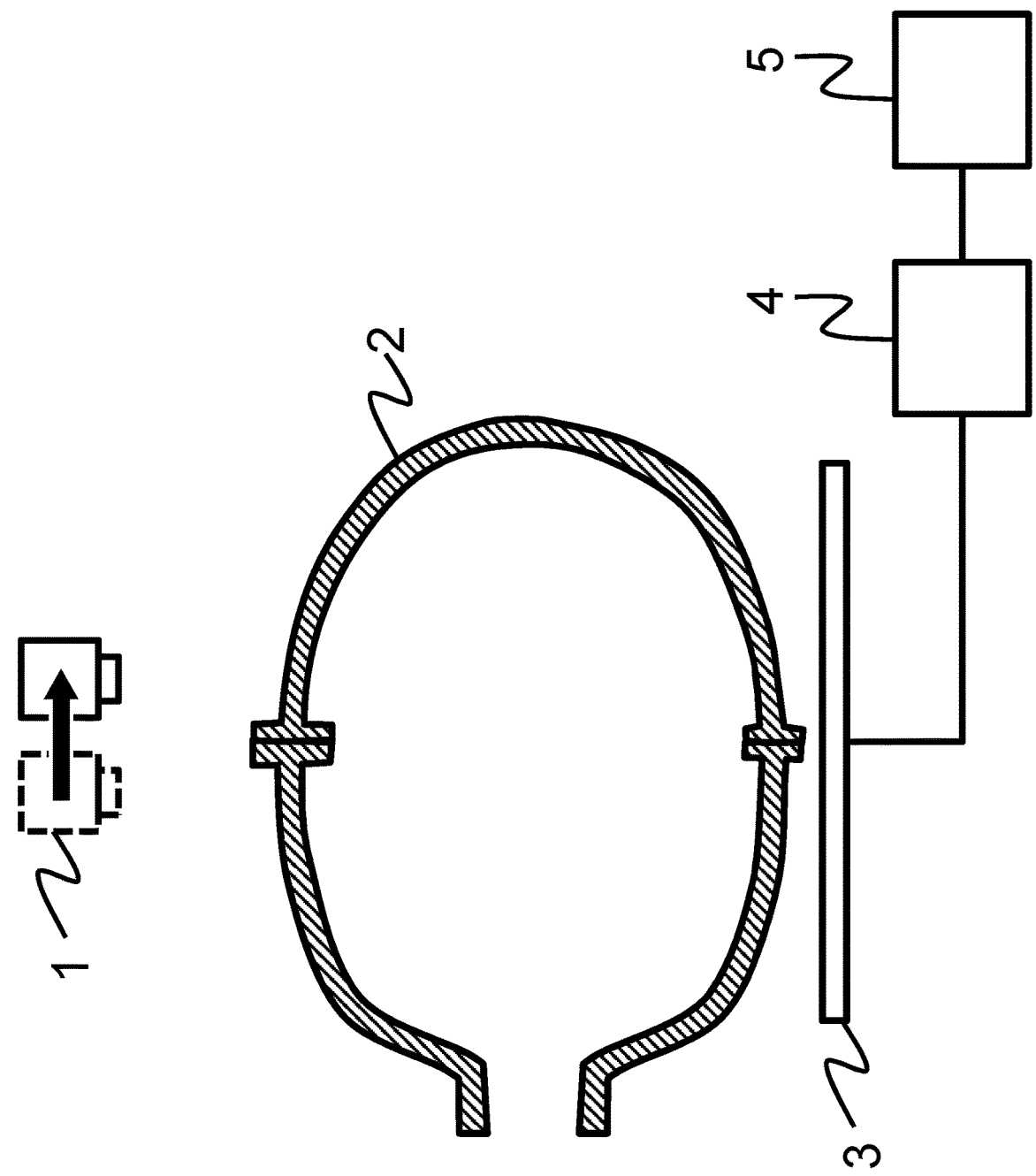
FIG. 11 is a schematic diagram for explaining a setup according to an embodiment of the present invention that is provided with a means for moving the X-ray emission means.

(1) A setup in which the X-ray emission means 1 is moved each time an X-ray beam is detected by the X-ray detection means 3 in order to provide a plurality of X-ray emitting paths. A schematic diagram is shown in FIG. 11. FIG. 11 is a schematic diagram for explaining a setup according to an embodiment of the present invention that is provided with a means of moving the X-ray emission means. The means for moving the X-ray emission means is preferably configured so that its moving direction is parallel to the X-ray detection means 3 and perpendicular to the joining interface.

Figure 12:
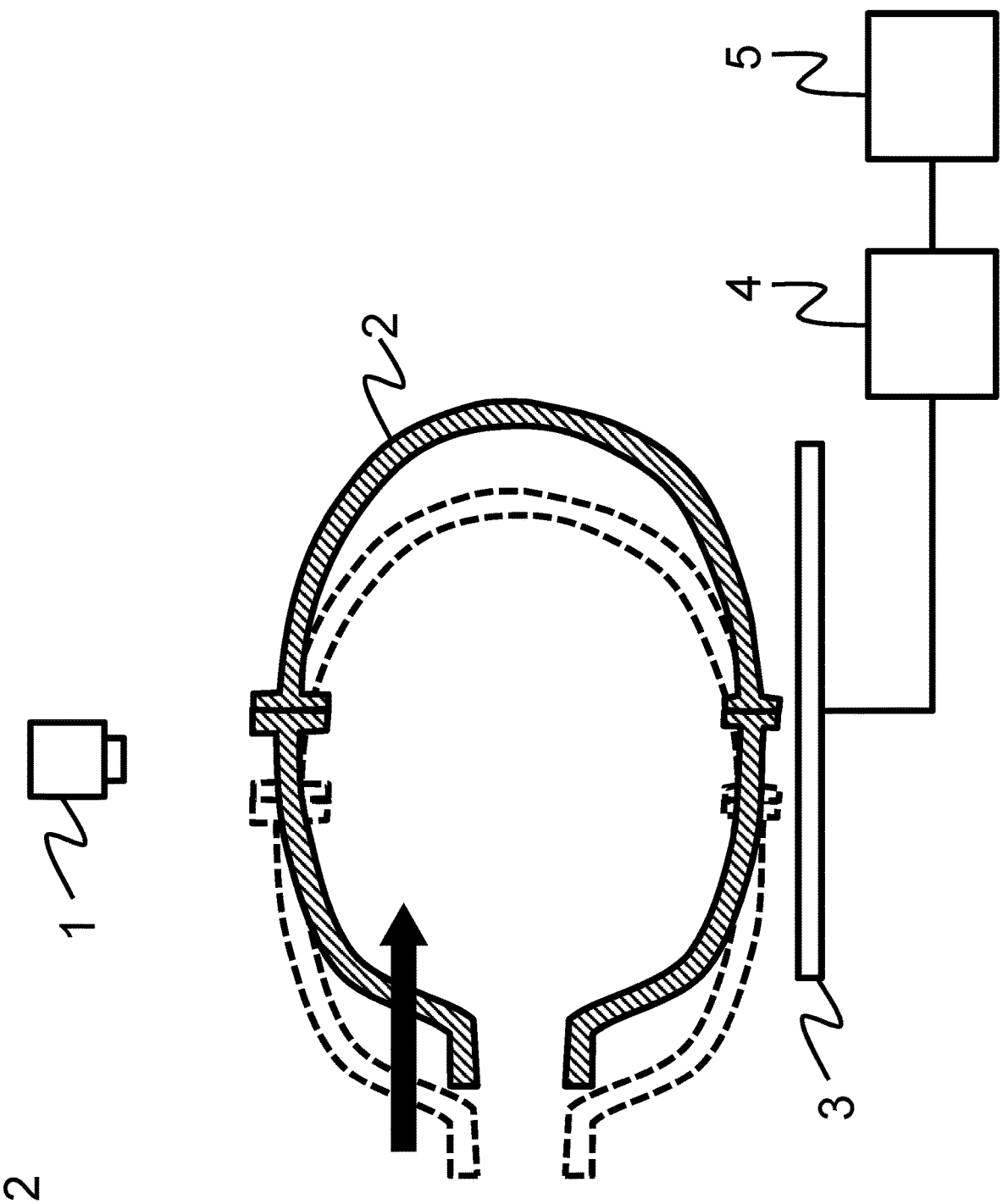
FIG. 12 is a schematic diagram for explaining an embodiment of the present invention that is provided with a means for moving the high pressure tank member.

(2) A setup in which the molded resin article 2 is moved each time an X-ray beam is detected by the X-ray detection means 3 in order to provide a plurality of X-ray emitting paths. A schematic diagram is shown in FIG. 12. FIG. 12 is a schematic diagram for explaining a setup according to an embodiment of the present invention that is provided with a means of moving the molded resin article 2. The means for moving the molded resin article 2 is preferably configured so that its moving direction is parallel to the X-ray detection means 3 and perpendicular to the arrival plane.

Furthermore, any of the embodiments of the present invention may be combined with a further modified embodiment such as described below.

Figure 13:
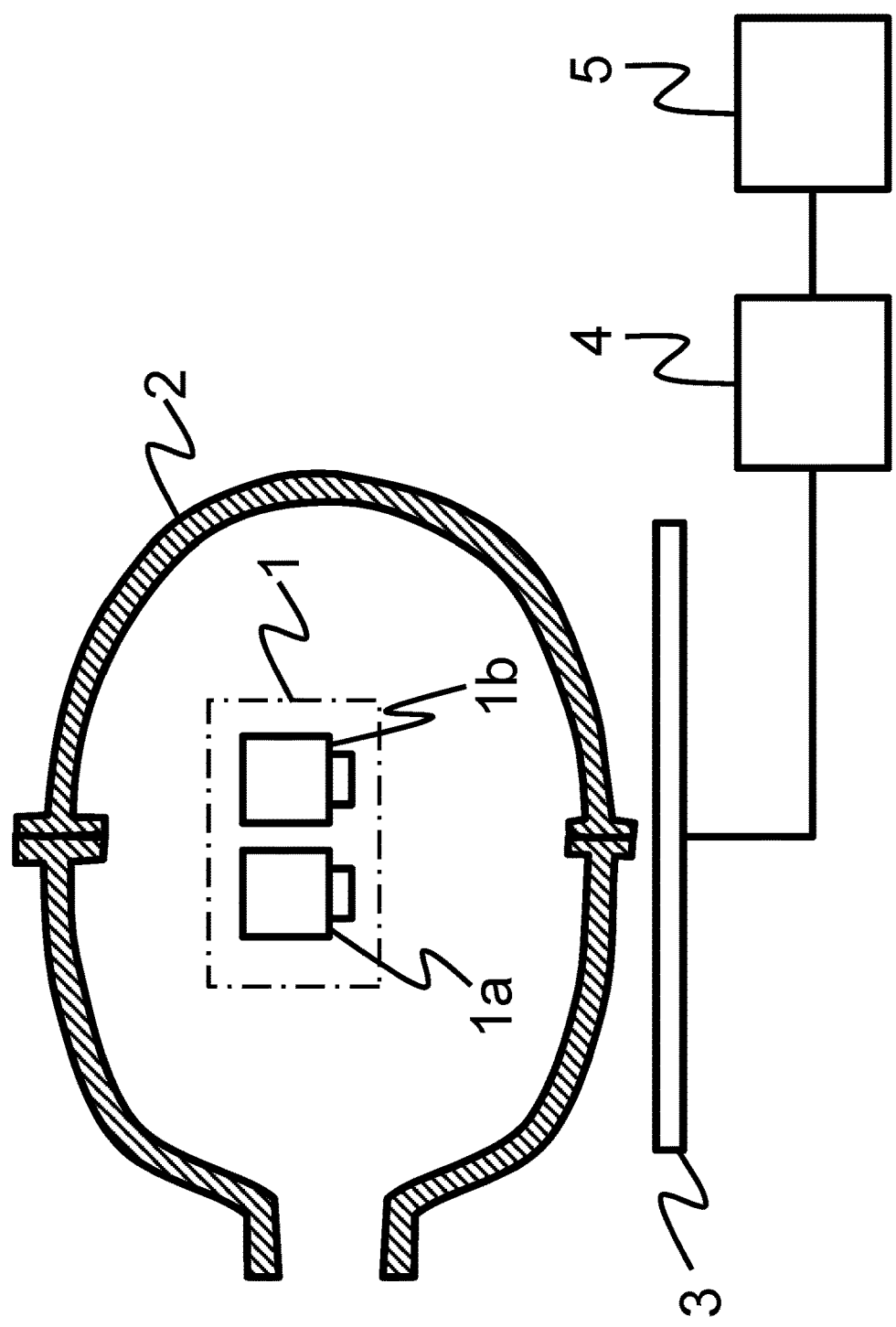
FIG. 13 is a schematic diagram for explaining other setup example 1 according to an embodiment of the present invention.

(1) A setup in which the X-ray emission means is located inside the molded resin article. A schematic diagram is shown in FIG. 13. This setup can be adopted when the X-ray emission means is small as compared with the opening of the molded resin article under inspection. In this setup, the emitted X-ray beams pass through only one layer of the molded resin article and accordingly suffer from less noise as compared with the case where the X-ray emission means 1 is located outside the molded resin article 2, thereby serving to realize a highly accurate inspection.

Figure 14:
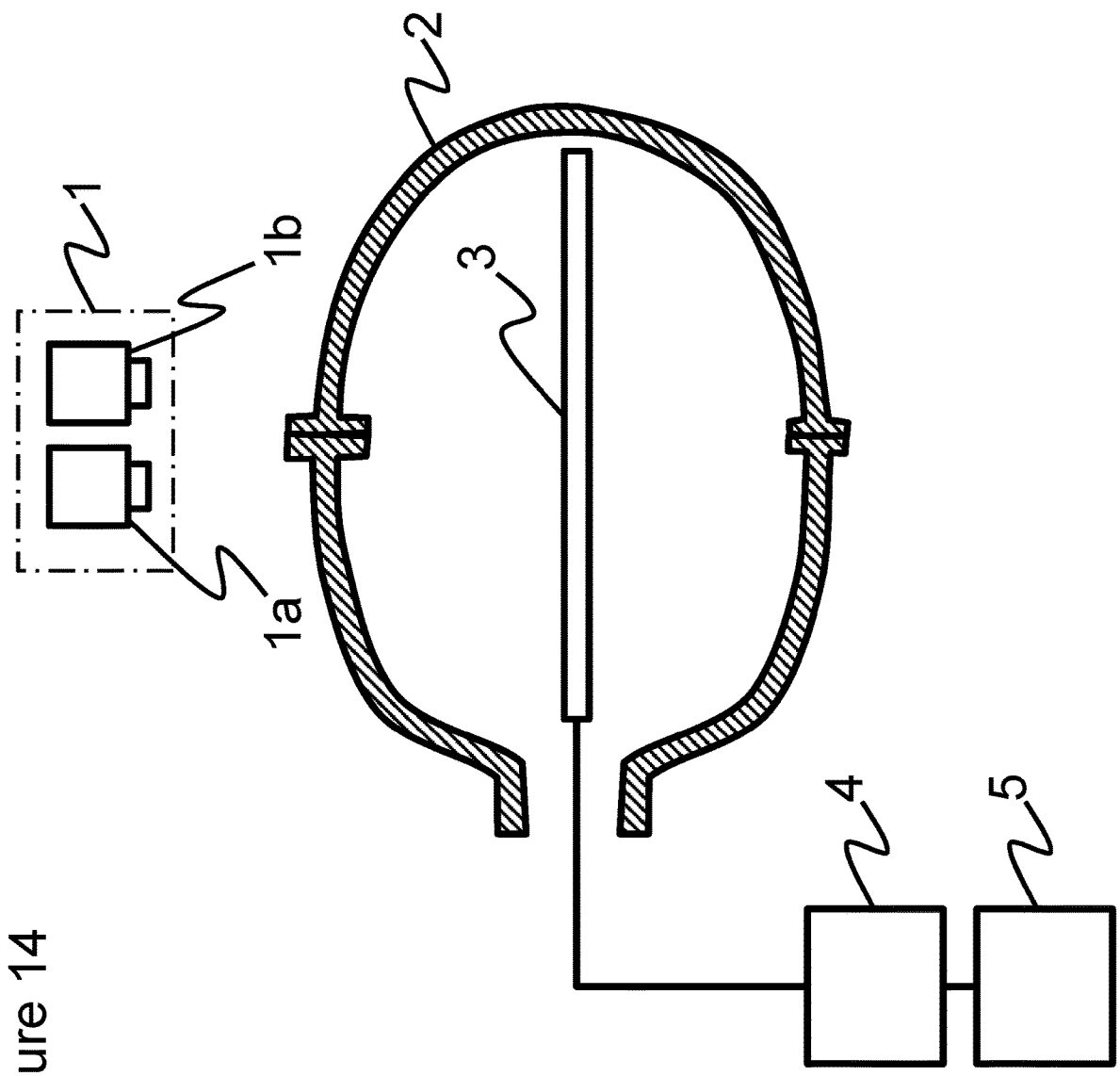
FIG. 14 is a schematic diagram for explaining other setup example 2 according to an embodiment of the present invention.

(2) A setup in which the X-ray detection means is located inside the molded resin article. A schematic diagram is shown in FIG. 14. This setup can be adopted when the X-ray detection means is small as compared with the opening of the molded resin article under inspection. In this setup, too, the emitted X-ray beams pass through only one layer of the molded resin article and accordingly suffer from less noise as compared with the case where the X-ray detection means 3 is located outside the molded resin article 2, thereby serving to realize a highly accurate inspection.

<Production Apparatus for Molded Resin Articles>

A production apparatus for molded resin articles according to an embodiment of the present invention is described below. The production apparatus for molded resin articles according to the present embodiment includes an inspection means having the molded resin article inspection apparatus described above and a selection means for distinguishing molded resin articles judged to be unacceptable by the inspection means from molded resin articles judged to be acceptable. It is described in detail below. The production apparatus for molded resin articles according to the present embodiment should at least include the inspection means and selection means, and there are no specific limitations on the other means. Accordingly, such other means as described below are mere examples which may be modified appropriately.

(Production Means for Molded Resin Articles)

This means is a production means for molded resin articles. For example, when the molded resin article is a liner member as described above, it may be manufactured by blow molding, injection molding, or the like as described above in relation to the embodiment representing an inspection apparatus for molded resin articles.

(Inspection Means)

The means includes an X-ray emission means for emitting X-ray beams through a plurality of paths, at least one X-ray detection means for detecting X-ray beams that have passed through a molded resin article, and an image processing means. A resin molded article found by the inspection means to contain impurities, voids, or the like is judged to be unacceptable and removed by the subsequent selection means.

(Selection Means)

This means is intended for distinguishing molded resin articles judged to be unacceptable by the inspection means from molded resin articles judged to be acceptable. This means may be implemented manually by a selector or implemented mechanically by a transport means that works in conjunction with a computer program that has information on acceptable or unacceptable articles. Acceptable molded resin articles that are not rejected by the selection means can be adopted as a material of high pressure tanks.

As described above, in the production method for molded resin articles according to the present embodiment, the inspection means can serve for appropriately detecting impurities and voids present in a molded resin article. In addition, a resin molded article found to contain impurities or the like is rejected and removed in the selection step. As a result, only acceptable molded resin articles can be selected out. A selected molded resin article may be subjected to subsequent steps and used to produce a high pressure tank. As a result, in the production method for molded resin articles according to the present embodiment, the subsequent steps can be omitted for unacceptable molded resin articles. Furthermore, this serves to increase the yield of high pressure tanks.

<Production Apparatus for High Pressure Tanks>

A production apparatus for high pressure tanks according to an embodiment of the present invention is described below. The high pressure tank production apparatus according to an embodiment of the present invention includes an inspection means having a molded resin article inspection apparatus as described above, a selection means for distinguishing molded resin articles judged to be unacceptable by the inspection means from molded resin articles judged to be acceptable, and an outer layer forming means for forming an outer layer for reinforcement on the molded resin articles judged to be acceptable. It is described in detail below. The production apparatus for high pressure tanks according to an embodiment of the present invention should at least include the inspection means, selection means, and outer layer forming means, and there are no specific limitations on other means. Accordingly, such other means as described below are mere examples which may be modified appropriately.

(Production Means for Molded Resin Articles)

This means is a production means for molded resin articles. For example, when the molded resin article is a liner member as described above, it may be manufactured by blow molding, injection molding, or the like as described above in relation to the embodiment representing an inspection apparatus for molded resin articles.

(Inspection Means)

The means includes an X-ray emission means for emitting X-ray beams through a plurality of paths, at least one X-ray detection means for detecting X-ray beams that have passed through a molded resin article, and an image processing means, and therefore, is identical to the inspection means described above in relation to the embodiment representing the production apparatus for molded resin articles.

(Selection Means)

This means is intended for distinguishing molded resin articles judged to be unacceptable by the inspection means from molded resin articles judged to be acceptable, and therefore, is identical to the selection means described above in relation to the embodiment representing the production apparatus for molded resin articles.

(Outer Layer Forming Means)

This means is intended to form a reinforcing outer layer (reinforcement layer) on a molded resin article judged to be acceptable. As described above in relation to the embodiment representing the inspection apparatus, the reinforcement layer is preferably a fiber reinforced resin layer, and one or more reinforcement layers are formed on the outer surface of the molded resin article. The molded resin article having a reinforcement layer is further equipped with a supply system (valve members, various piping systems, etc.) for supplying high pressure gas to the fuel cell as appropriate to serve as a high pressure tank.

As described above, in the production apparatus for high pressure tanks according to an embodiment of the present invention, the inspection apparatus can serve for appropriately detecting impurities and voids present in a molded resin article. In addition, a resin molded article found to contain impurities or the like is rejected and removed by the selection means. This means is intended to form a reinforcement layer only on a molded resin article judged to be acceptable. Therefore, when using the production apparatus for high pressure tanks according to an embodiment of the present invention, no reinforcement layer will be formed on a molded resin article that has been judged to be unacceptable, thereby serving, for example, for avoiding the wasting of fiber reinforced resin. Furthermore, this serves to increase the yield of high pressure tanks.

<Molded Resin Articles>

The molded resin articles according to the present invention are described below. The molded resin articles according to an embodiment of the present invention are produced by using a production apparatus for molded resin articles as described above. They are described in detail below. For the molded resin articles according to an embodiment of the present invention, it is only necessary to use a production apparatus as described above, and there are no specific limitations on other means. Accordingly, such other means as described below are mere examples which may be modified appropriately.

(Production Apparatus for Molded Resin Articles)

This apparatus is a production apparatus for molded resin articles. This is identical to the production apparatus for molded resin articles described above.

Thus, when producing a molded resin article according to an embodiment of the present invention, the production apparatus can serve for appropriately detecting impurities and voids present in a molded resin article. In addition, a resin molded article found to contain impurities or the like is rejected and removed by the selection means. Therefore, when producing a molded resin article according to an embodiment of the present invention, no reinforcement layer will be formed on a molded resin article that has been judged to be unacceptable, thereby serving, for example, for avoiding the wasting of fiber reinforced resin. Furthermore, this serves to increase the yield of high pressure tanks.

Thus, when producing a molded resin article according to an embodiment of the present invention, the molded resin article is selected out only when it is an acceptable one. A selected molded resin article will be subjected to subsequent steps and used to produce a high pressure tank. As a result, when producing a molded resin article according to an embodiment of the present invention, the subsequent steps can be omitted for unacceptable molded resin articles.

<High Pressure Tank>

A high pressure tank according to an embodiment of the present invention is described below. The high pressure tank according to an embodiment of the present invention is produced by using the above-mentioned production apparatus for high pressure tanks. It is described in detail below. For the high pressure tank according to an embodiment of the present invention, it is only necessary to use a production apparatus as described above, and there are no specific limitations on other means. Accordingly, such other means as described below are mere examples which may be modified appropriately.

(Production Apparatus for High Pressure Tanks)

This apparatus is a production apparatus for high pressure tanks. This is identical to the production apparatus for high pressure tanks described above.

Thus, when using the high pressure tank according to an embodiment of the present invention, a reinforcement layer is formed only on a molded resin article judged to be acceptable. Therefore, when using a pressure tank according to an embodiment of the present invention, no reinforcement layer will be formed on a molded resin article that has been judged to be unacceptable, thereby serving, for example, for avoiding the wasting of fiber reinforced resin.

<Fuel Cell Vehicle>

A fuel cell vehicle according to an embodiment of the present invention is described below. The fuel cell vehicle according to an embodiment of the present invention uses a high pressure tank as described above. It is described in detail below. Here, for the fuel cell vehicle according to an embodiment of the present invention, it is only necessary to use a high pressure tank as described above, and there are no specific limitations on other means. Accordingly, such other means as described below are mere examples which may be modified appropriately.

(High Pressure Tank)

This tank is a high pressure tank. This is identical to the high pressure tank described above.

Thus, when producing a fuel cell vehicle according to an embodiment of the present invention, a reinforcement layer is formed only on a molded resin article judged to be acceptable and a high pressure tank produced therefrom is used. Therefore, when producing a fuel cell vehicle according to an embodiment of the present invention, the use of an unacceptable high pressure tank is prevented, thereby serving, for example, for avoiding the wasting of other members for the fuel cell vehicle.

EXPLANATION OF NUMERALS

1 X-ray emission means
1a X-ray emission means
1b X-ray emission means
2 molded resin article
3 X-ray detection means
4 image processing means
5 selection means
6 void defect in joint portion
7 void defect in burr
8 reference marker
9 erroneous detection region
10a X-ray detection image a given by X-ray emission means 1a
10b X-ray detection image b given by X-ray emission means 1b
11 defect candidate image
12 stereo matching image
13 height position calculation image
14 defect selection result image

The invention claimed is:

1. A molded resin article inspection apparatus comprises an X-ray emitting apparatus for emitting X-ray beams through a plurality of paths, one or more X-ray detectors for detecting X-ray beams that have passed through a molded resin article, a height measuring means for measuring height at a reference marker on the molded resin article, a distance measuring means for measuring the distance from the X-ray emitting apparatus to the molded resin article, and an image processor, wherein the image processor is configured for detecting defect candidates based on two or more images acquired by the X-ray detector, using a stereo matching method, performing logical multiplication of the image having recorded height position information and a defect candidate image, and judging the state of the defects candidate from the height position, wherein the image processor is also configured for setting the distance from the X-ray emitting apparatus to the molded resin article, setting an inspection range based on the distance and the thickness of the molded resin article, and deciding that a defect candidate found in the inspection range is a defect, and wherein the image processor is further configured for inputting a target distance from the X-ray emitting apparatus to the molded resin article, calculating the difference between the input value and the measured value, and making a correction based thereon so that the distance becomes equal to the input value.

2. A molded resin article inspection apparatus as set forth in claim 1, wherein the X-ray emitting apparatus comprises one or more X-ray emitting apparatus and an X-ray emitting position moving means for moving the one or more X-ray emitting apparatus so that X-ray beams are emitted from two or more different positions towards the molded resin article.

3. A molded resin article inspection apparatus as set forth in claim 1, wherein the X-ray emitting apparatus comprises one or more X-ray emitting apparatus and a means for moving the molded resin article to two or more positions.

4. A molded resin article inspection apparatus as set forth in claim 1, wherein the resin molded article is a member of a high pressure tank.

5. A production apparatus for molded resin articles having the molded resin article inspection apparatus as set forth in claim 1, the production apparatus being configured for distinguishing molded resin articles judged to be unacceptable by the molded resin article inspection apparatus from molded resin articles judged to be acceptable.

6. A production apparatus for high pressure tanks having the molded resin article inspection apparatus as set forth in claim 1, the production apparatus being configured for distinguishing molded resin articles judged to be unacceptable by the molded resin article inspection apparatus from molded resin articles judged to be acceptable, and means for forming an outer layer for reinforcement on the molded resin articles judged to be acceptable.

7. A molded resin article inspection apparatus as set forth in claim 1, wherein the height measuring means and the distance measuring means are each selected from the group consisting of laser triangulation type displacement meter, laser interferometer, ultrasonic range finder, eddy current type displacement sensor, and stylus type displacement meter.

8. An inspection method for molded resin articles designed to emit X-ray beams through a plurality of paths, detect X-ray beams transmitted through a molded resin article at one or more positions, detect a defect candidate in a detected X-ray image, measure the height by a stereo matching method, perform logical multiplication of the resulting height information image and the image obtained as a defect candidate, and judge the state of the defect candidate based on the height position, wherein the selection method is designed to set a distance from the X-ray emitting position to the molded resin article, set an inspection range based on the distance and the thickness of the molded resin article, and decide that a defect candidate found in the inspection range is a defect, and wherein the distance setting method is designed to input a target distance fro the X-ray emitting position to the molded resin article, measure the distance from the X-ray emitting position to the molded resin article, and calculate the difference between the input distance value and the measured distance value to make a correction based thereon so that the distance becomes equal to the input value.

9. A molded resin article inspection method as set forth in claim 8, wherein the method for emitting X-ray beams through a plurality of paths is designed to move the X-ray emitting position so that X-ray beams are emitted from two or more different positions towards the molded resin article.

10. A molded resin article inspection apparatus as set forth in claim 8, wherein the X-ray emitting apparatus is designed to emit X-ray beams from one or more positions and move the molded resin article to two or more positions.

11. A molded resin article inspection method as set forth in claim 8, wherein the resin molded article is a member of a high pressure tank.

12. A production method for molded resin articles having a molded resin article inspection method as set forth in claim 8, comprising an inspection step using the molded resin article inspection method and a selection step for distinguishing molded resin articles judged to be unacceptable by the inspection means from molded resin articles judged to be acceptable.

13. A production method for high pressure tanks that uses a molded resin article inspection method as set forth in claim 8, comprising an inspection step using the molded resin article inspection method, a selection step for distinguishing molded resin articles judged to be unacceptable in the inspection step from molded resin articles judged to be acceptable, and an outer layer forming step for forming an outer layer for reinforcement on the molded resin articles judged to be acceptable.

14. A production method for fuel cell vehicles that uses a molded resin article inspection method as set forth in claim 8, comprising an inspection step using the molded resin article inspection method, a selection step for distinguishing molded resin articles judged to be unacceptable in the inspection step from molded resin articles judged to be acceptable, an outer layer forming step for forming an outer layer for reinforcement on the molded resin articles judged to be acceptable in order to provide a high pressure tank, and an installation step for installing the resulting high pressure tank on a chassis.

* * * * *